(12) United States Patent
Dabney

(10) Patent No.: US 9,579,177 B2
(45) Date of Patent: *Feb. 28, 2017

(54) DENTAL AND MEDICAL DEVICES WITH LIGHT SOURCE AND ANTIMICROBIAL SOLUTION

(71) Applicant: Paul Dabney, Georgetown, TX (US)

(72) Inventor: Paul Dabney, Georgetown, TX (US)

(73) Assignee: DABNEY PATENTS, L.L.C., Georgetown, TX (US)

( * ) Notice: Subject to any disclaimer, the term of this patent is extended or adjusted under 35 U.S.C. 154(b) by 201 days.

This patent is subject to a terminal disclaimer.

(21) Appl. No.: 14/497,269

(22) Filed: Sep. 25, 2014

(65) Prior Publication Data

US 2016/0015494 A1  Jan. 21, 2016

Related U.S. Application Data

(60) Provisional application No. 62/026,498, filed on Jul. 18, 2014.

(51) Int. Cl.
*A61C 19/06* (2006.01)
*A61C 1/08* (2006.01)
(Continued)

(52) U.S. Cl.
CPC .............. *A61C 19/06* (2013.01); *A61C 1/088* (2013.01); *A61C 19/063* (2013.01); (Continued)

(58) Field of Classification Search
CPC ....... A61C 19/06; A61C 19/063; A61C 1/088; A61M 5/445; A61M 25/0043;
(Continued)

(56) References Cited

U.S. PATENT DOCUMENTS 6,247,930 B1  6/2001 Chiang
7,320,594 B1  1/2008 Rizoiu
(Continued)

OTHER PUBLICATIONS

Osnat Feuerstein, Daniel Moreinos and Doron Steinberg, Synergic antibacterial effect between visible light and hydrogen peroxide on *Streptococcus mutans*, Journal of Antimicrobial Chemotherapy, 2006, p. 872-876, vol. 57, Oxford University Press, U.K.

*Primary Examiner* — Rex R Holmes
(74) *Attorney, Agent, or Firm* — Maier & Maier, PLLC

(57) ABSTRACT

Dental and medical devices with a light source and antimicrobial solution include an antimicrobial solution; a fiber optic cable that exposes the antimicrobial solution to light of a predetermined wavelength; and a solution holding apparatus that retains the lighted antimicrobial solution against the tissue. A method for antimicrobial treatment of a user includes retaining an antimicrobial solution in a solution holding apparatus; purposefully selecting a wavelength of light that reacts with the antimicrobial solution; providing the selected wavelength of light from an LED or laser or other appropriate light source; utilizing a fiber optic cable to expose the antimicrobial solution to the light; and utilizing the solution holding apparatus to hold the lighted antimicrobial solution against the user.

19 Claims, 3 Drawing Sheets

(51) Int. Cl.
    *A61K 31/203* (2006.01)
    *A61K 31/60* (2006.01)
    *A61K 31/65* (2006.01)
    *A61K 31/7048* (2006.01)
    *A61K 31/7056* (2006.01)
    *A61K 33/40* (2006.01)
    *A61K 47/22* (2006.01)
    *A61M 5/44* (2006.01)
    *A61M 25/00* (2006.01)
    *A61N 5/06* (2006.01)
    *A61N 5/067* (2006.01)

(52) U.S. Cl.
    CPC .......... *A61K 31/203* (2013.01); *A61K 31/60* (2013.01); *A61K 31/65* (2013.01); *A61K 31/7048* (2013.01); *A61K 31/7056* (2013.01); *A61K 33/40* (2013.01); *A61K 47/22* (2013.01); *A61M 5/445* (2013.01); *A61M 25/0043* (2013.01); *A61N 5/0616* (2013.01); *A61M 2025/0056* (2013.01); *A61N 2005/063* (2013.01); *A61N 2005/0606* (2013.01); *A61N 2005/067* (2013.01); *A61N 2005/0645* (2013.01); *A61N 2005/0651* (2013.01); *A61N 2005/0653* (2013.01); *A61N 2005/0662* (2013.01)

(58) Field of Classification Search
    CPC .......... A61N 5/0616; A61N 2005/0662; A61K 33/40; A61K 31/65; A61K 31/7056; A61K 47/22; A61K 31/7048; A61K 31/203; A61K 31/60
    See application file for complete search history.

(56) References Cited

U.S. PATENT DOCUMENTS

| | | | |
|---|---|---|---|
| 7,597,556 B1 | 10/2009 | Harrison | |
| 8,439,674 B2 * | 5/2013 | Li | A61C 19/063 433/24 |
| 8,591,229 B2 * | 11/2013 | Keller | A61C 19/063 433/80 |
| 2003/0198605 A1 * | 10/2003 | Montgomery | A61O 5/00 424/53 |

* cited by examiner

DENTAL AND MEDICAL DEVICES WITH LIGHT SOURCE AND ANTIMICROBIAL SOLUTION

RELATED APPLICATIONS

This application claims the benefit of the filing date of U.S. Patent Application No. 62/026,498, filed Jul. 18, 2014, which is incorporated herein by reference in its entirety.

BACKGROUND OF THE INVENTION

The present invention generally relates to enhancement of antimicrobial solutions and more specifically to dental and medical devices with a light source and antimicrobial solutions.

Microbes exist that cause harm or disease in living tissues.

Light of certain wavelengths has been demonstrated to improve or "super-charge" the effects of certain antimicrobial or anti-microbial agents, creating a synergistic effect to destroy or inhibit microbial growth.

Most chemical reactions work best at a certain temperature. These ideal temperatures vary for each reaction. A "scalding chart" might indicate that water of 130 degrees is safe under an exposure of 30 seconds, but over that it causes burns. Water of 120 degrees may be safe up to 5 minutes.

It would be desirable to add light of certain wavelengths to a device that holds certain antimicrobial agents in close proximity to tissues, so a synergistic effect can be created to destroy or inhibit microbial growth on the tissues.

SUMMARY OF THE INVENTION

In one aspect of the present invention, a device for antimicrobial treatment of a tissue of a user includes an antimicrobial solution; a fiber optic cable that exposes the antimicrobial solution to light of a predetermined wavelength; and a solution holding apparatus that retains the lighted antimicrobial solution against the tissue.

In another aspect of the present invention, a device for antimicrobial treatment of a tooth of a user includes an antimicrobial solution; a fiber optic cable that exposes the antimicrobial solution to a predetermined wavelength of light; a dental tray that retains the antimicrobial solution in a cavity on a side of the tray, retains the fiber optic cable, and holds the lighted antimicrobial solution against the tooth; an external light source that utilizes either a light emitting diode (LED), laser, or any effective light source to provide the light of a predetermined wavelength; and a fiber optic connection cable that optically connects the light source with the fiber optic cable.

In yet another aspect of the present invention, a method for antimicrobial treatment of a user includes retaining an antimicrobial solution in a solution holding apparatus; purposefully selecting a wavelength of light that reacts with the antimicrobial solution; providing the selected wavelength of light from an LED, laser or any effective light source; utilizing a fiber optic cable to expose the antimicrobial solution to the light; and utilizing the solution holding apparatus to hold the lighted antimicrobial solution against the user.

DETAILED DESCRIPTION

Figure 1:
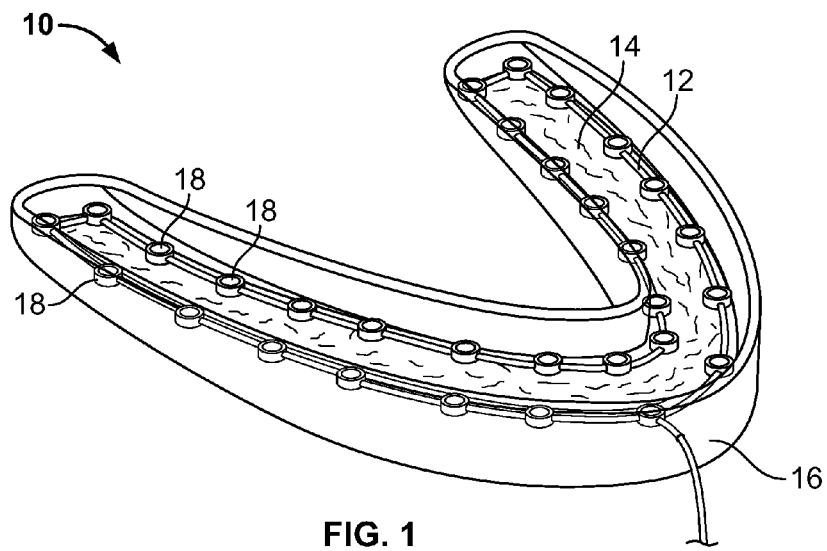
FIG. 1 depicts an embodiment of the present invention.

The preferred embodiment and other embodiments, which can be used in industry and include the best mode now known of carrying out the invention, are hereby described in detail with reference to the drawings. Further embodiments, features and advantages will become apparent from the ensuing description, or may be learned without undue experimentation. The figures are not necessarily drawn to scale, except where otherwise indicated. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order.

An embodiment of the present invention generally provides a device to hold solutions in contact with tissues, such as flesh or teeth, while the tissues and solutions are simultaneously being exposed to certain wavelengths of light. This device has a component that amplifies the effect of the antimicrobial solutions by using a certain wavelength of light. The antimicrobial solution may or may not be light activated at any given time. When the light is on, the solution is "supercharged" by the light. This synergistic effect eliminates or reduces more microbes than the solution acting alone.

Microbes exist that cause harm or disease in living tissues. By adding a light of certain wavelengths to a device that holds certain antimicrobial agents in close proximity to tissues, a synergistic effect can be created to destroy or inhibit microbial growth. In the oral cavity, this device could be a tray designed to cover the teeth and gingival. This tray would emit certain wavelengths of light that when combined with certain antimicrobial solutions in the tray would cause a synergistic antimicrobial effect. The light could be produced, for example, from a light emitting diode (LED) or laser. An external light source could be connected to the fiber optic cable in the solution holding apparatus with a fiber optic connection cable that may also include a fiber optic connection interface or plug.

Embodiments of the present invention may create another means to treat disease. Super charging antimicrobial solutions with certain wavelengths of lights may cause the solutions to eliminate or reduce microbes at a higher percentage than the solution alone.

Embodiments may create a synergistic effect between certain wavelengths of light and antimicrobial solutions that when applied to tissues eliminates or reduces disease causing microorganisms.

Embodiments of the present invention may consist of a solution holding apparatus or medium that emits certain wavelengths of light into the solution. When this light and solution combination is applied to tissues, a synergistic effect is created that reduces or eliminates microorganisms that cause disease. The essential components are 1. The solution holding apparatus 2. A light source 3. An antimicrobial solution.

Embodiments may utilize blue light, or another certain predetermined wavelength of light that supercharges the solution, with an exposure from a few second to minutes.

Embodiments may also use an H2O2 solution, such as a gel, with concentration of 0.3 mM or any concentration of solution that is suitable as an antimicrobial agent.

In an embodiment, for safety, a "scalding chart" might indicate that water of 130 degrees is safe under an exposure of 30 seconds, but over that it causes burns. Water of 120 degrees may be safe up to 5 minutes. Hydrogen peroxide (H2O2), when it is exposed to a light of 400-500 nanometers wavelength, may kill 96% of microbes in less than 20 seconds. This solution may work best at 57 degrees Celsius (134 degrees F.).

Alternate embodiments may include heating elements that warm and further super-charge the antimicrobial solution. In embodiments, a device may contain heating or cooling components or both. In an embodiment, an antimicrobial solution may be preheated to an ideal temperature before it is exposed to synergizing light. For example, Hydrogen peroxide may preferably be exposed to a light of 400-500 nanometers at 57 degrees Celsius (134 degrees F.) for less than 20 seconds. Other chemicals may have different preferred temperatures.

In an embodiment, a chemical may be used without a reservoir. The chemical may be inserted directly into the body cavity and exposed to light by a fiber optic wand with a plurality of light emitting fibers. Embodiments of a carrier or reservoir may be the solution itself or a gel. This gel could be inserted in a body cavity with a catheter and exposed to the synergizing light by the same catheter or a different catheter. Delivery devices may include, but are not limited to, reservoirs, bandages, gels, solutions, head coverings, wraps, socks, stockings, hats, helmets, mists, suits, tents, probes, or catheters.

Further embodiments that retain a microbial solution and hold the solution against a portion of the user's body may include: bandage; a bucket; a body suit; a catheter; a helmet; a bowl; and a body part covering. Still further embodiments include methods for using and applying said devices to provide anti-bacterial treatment.

An embodiment of a tray for either upper or lower teeth of a user may be like a sports mouth guard, with an open top to be pressed around the teeth. The solution may be a gel, so that it can be retained in a tray for the lower teeth as well as a tray for the upper teeth. An embodiment may have two trays connected together to form a dual tray for simultaneous treatment of upper and lower teeth.

To make an embodiment, one could embed light emitting fiber optic fibers in a generally C-shaped dental tray that can hold certain antimicrobial solutions in a cavity on one side of the tray. A light source of certain wavelengths may be connected to the fiber optic fibers. The tray may be made of waterproof, safe material, such as plastic. The dental tray may be shaped by making an impression of the user's teeth, making a model from the impression, and then molding the tray over the model. The fiber optic cable may be embedded or inserted into the tray before or after the tray is molded. Light emitting elements on the cable may be added after the user's teeth have been measured to help align the elements or light terminations with the corners of the user's teeth.

The light terminations may be positioned on the fiber optic cable within the tray before use so that each light termination is located between adjacent teeth or adjacent to a tooth of the user. When the light source is activated, a synergistic effect may be created that causes the antimicrobial solution to become more effective than the solution without the light.

A side light emitting cable may be composed of one or more strands of fiber optic cable. The cable may have a clear coating or a partially-translucent coating, or the cable may have an opaque coating that is partially removed, such as along one side of the cable. The diameter of the cable may vary.

An embodiment of a device that covers a user's teeth and gingival, may include a tray that retains a microbial solution and holds the solution against the teeth and gingival; and a light source that emits a predetermined wavelength of light into the solution. Another embodiment of a device for a portion of a user's body may include a bandage or other device that retains a microbial solution and holds the solution against the portion of the user's body; and a light source that emit a predetermined wavelength of light into the solution.

FIG. 1 depicts an embodiment of a dental device 10. A light emitting fiber optic cable 12 may expose the antimicrobial solution 14 to a certain wavelength of light, such as a purposefully selected wavelength or frequency of light from an LED or laser. A tray 16 may hold the antimicrobial solution 14. An embodiment may include a plurality of light terminations 18 or other light emitters on the light emitting fiber optic cable 12. Each light termination 18 taps into the fiber optic cable 12 to pipe some of the light out the top of the termination, thereby emitting light into the antimicrobial solution 14. The device may be adjustable, so that the terminations 18 can added or moved, or the quantity and locations of the light terminations 18 may be measured to fit an individual user. The light terminations 18 may be located within the tray 16 so that each light termination 18 is will be positioned between adjacent teeth or adjacent to a tooth of the user. The fiber optic cable may be opaque with light emitters spaced along its length, or may be at least partially translucent to emit light along its length.

In an embodiment, a the fiber optic cable 12 may connect to a light source 20 through a fiber optic connection cable 22. The connection cable 22 may enter the tray 16 and optically connect with the fiber optic cable 12 through a fiber optic connection interface 24 so that the light source 20 can be attached and removed after use. An embodiment of the interface 24 may include an aperture in a wall of the tray 16 with a fiber optic connection cable 22 fixed to the fiber optic cable 12. Another embodiment of the interface 24 may include a socket on the tray 16 that mates with a plug on the connection cable 22 so that the light source 20 can be attached and removed after use.

Figure 2:
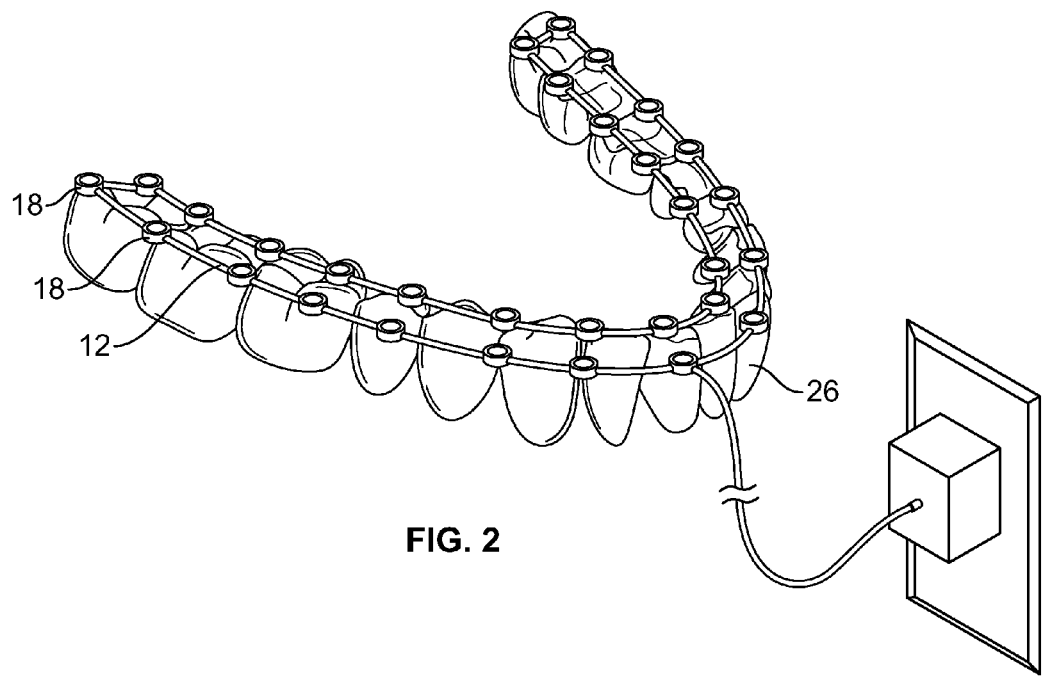
FIG. 2 depicts an embodiment of the present invention in use.

As depicted in the embodiment of FIG. 2, an embodiment may be installed on an arch of human teeth. A user may have a lower row of teeth 26 having, for example, 14 teeth if 2 wisdom teeth have been removed. An embodiment of a device for this user may have 30 light terminations 18 or other light emitters connected to the fiber optic cable 12 in two rows of 15 each, so that there will be 4 terminations located at the corners of each tooth that surround the tooth with light emitters.

Figure 3:
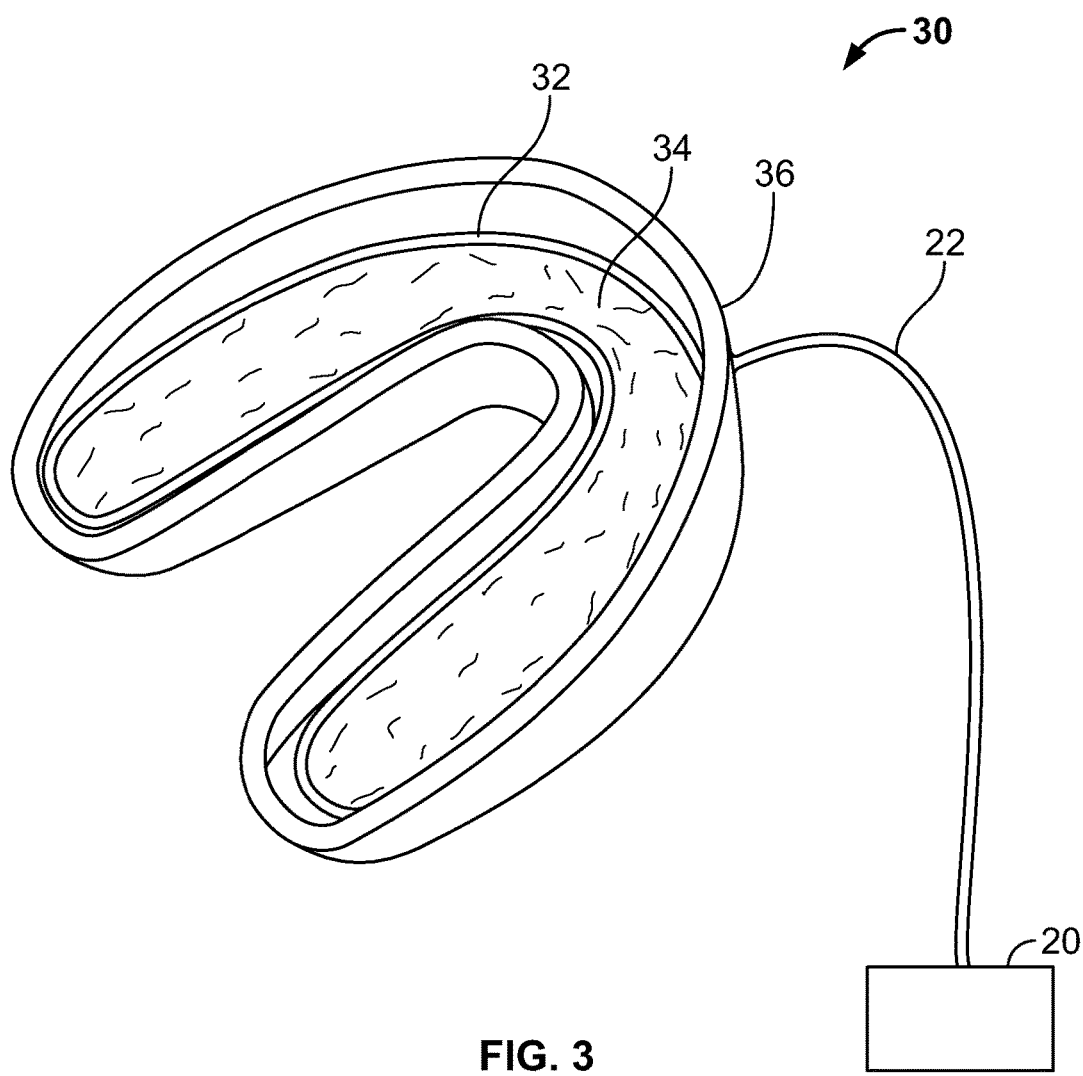
FIG. 3 depicts another embodiment of the present invention.

FIG. 3 depicts another embodiment of a dental device 30. A light emitting fiber optic cable 32 may expose the antimicrobial solution 34 to a certain wavelength of light. A tray 36 may hold the antimicrobial solution 34. An embodiment may include a translucent or side-lighting fiber optic cable 32 to emit light along its length. The fiber optic cable 32 may connect to a light source 20 through a fiber optic connection cable 22.

Figure 4A:
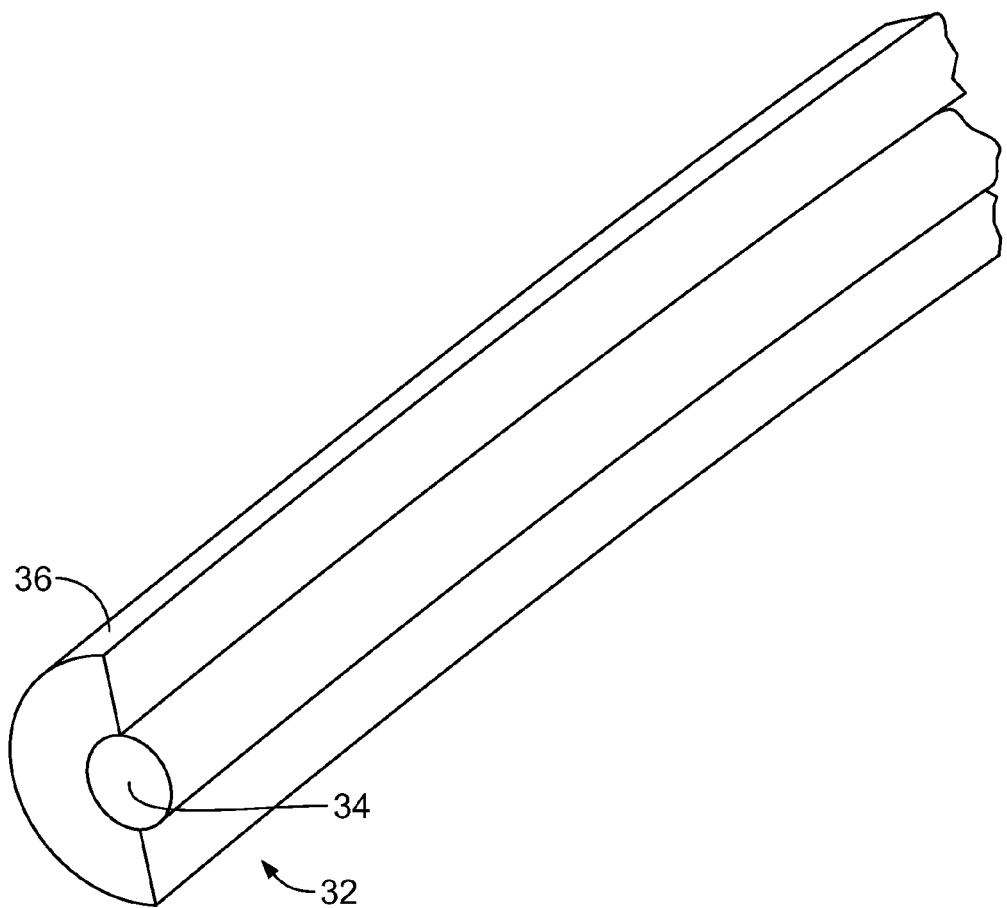
FIGS. 4A and 4B depict an embodiment of a side-lighting cable according to the present invention.

FIG. 4A depicts an embodiment of a side-lighting fiber optic cable that includes a light-emitting inner core 34 and an outer shield 36 or coating. The outer shield 36 may be opaque, or partially translucent. The outer shield 36 only covers part of the light-emitting inner core 34 so that more light will be directed to the side. One side of the shielding may be removed to expose light down its length, similar to a banana with just one piece of peel removed.

Figure 4B:
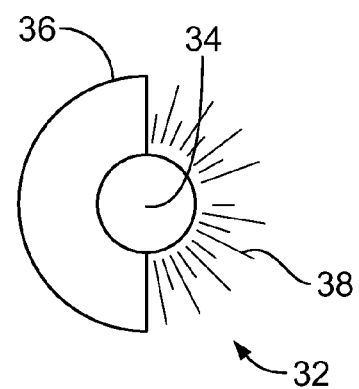

As depicted in the embodiment of FIG. 4B, the side-lighting fiber optic cable 32 may be emit light 38 of a certain wavelength or frequency to the side of the cable.

An embodiment may include a device that covers a user's teeth and gingival, including a tray that retains a microbial solution and holds the solution against the teeth and gingival; and a light source that emits a predetermined wavelength of light into the solution. An embodiment may include a device for a portion of a user's body, including a bandage that retains a microbial solution and holds the solution against the portion of the user's body; and a light source that emit a predetermined wavelength of light into the solution.

I claim:

1. A device for antimicrobial treatment of a tissue of a user, the device comprising:
    an antimicrobial solution;
    a fiber optic cable that exposes the antimicrobial solution to light of a predetermined wavelength; and
    a solution holding apparatus that retains the lighted antimicrobial solution against the tissue, wherein the fiber optic cable is disposed on a surface of the solution holding apparatus proximate the tissue.

2. The device of claim 1, further comprising:
    a plurality of light terminations on the fiber optic cable that emit light from the fiber optic cable into the antimicrobial solution.

3. The device of claim 1, wherein the fiber optic cable includes a light-emitting inner core and an outer shield that only covers part of the light-emitting inner core so that the light will be directed to the side.

4. The device of claim 1, further comprising:
    a light source that utilizes a light emitting diode (LED) to provide the light of a predetermined wavelength.

5. The device of claim 1, further comprising:
    a light source that utilizes a laser to provide the light of a predetermined wavelength.

6. The device of claim 1, further comprising:
    an external light source to provide the light of a predetermined wavelength; and
    a fiber optic connection cable that optically connects the light source with the fiber optic cable.

7. The device of claim 6, further comprising:
    a socket on the solution holding apparatus that mates with a plug on the fiber optic connection cable so that the light source may be attached and removed.

8. The device of claim 1, wherein the solution holding apparatus includes a dental tray that retains the antimicrobial solution in a cavity on a side of the tray, the fiber optic cable is retained within the tray, the tissue is a tooth of the user, and the tray is shaped to hold the lighted antimicrobial solution against the tooth.

9. The device of claim 1, wherein the solution holding apparatus includes a dental tray that retains the antimicrobial solution in a cavity on a side of the tray, the fiber optic cable is retained within the tray, the tissue is a plurality of teeth of the user, each of the teeth having two opposite sides, and the tray is shaped to hold the lighted antimicrobial solution against the plurality of teeth;
    and the device further comprises:
    a plurality of light terminations on the fiber optic cable that emit light from the fiber optic cable into the antimicrobial solution, the light terminations being positioned and of sufficient quantity so that there is at least one light termination adjacent to each of the two opposite sides of each tooth.

10. The device of claim 1, wherein the antimicrobial solution is a gel that includes hydrogen peroxide (H2O2).

11. The device of claim 1, wherein the predetermined wavelength of light is between 400 and 500 nanometers.

12. The device of claim 1, further comprising:
    a heating element in the solution holding apparatus that warms the antimicrobial solution.

13. A device for antimicrobial treatment of a tooth of a user, the device comprising:
    an antimicrobial solution;
    a fiber optic cable that exposes the antimicrobial solution to a predetermined wavelength of light;
    a dental tray that retains the antimicrobial solution in a cavity on a side of the tray, retains the fiber optic cable on surface of the tray proximate the tooth, and holds the lighted antimicrobial solution against the tooth;
    an external light source that provides the light of a predetermined wavelength; and
    a fiber optic connection cable that optically connects the light source with the fiber optic cable.

14. The device of claim 13, further comprising:
    a plurality of light terminations on the fiber optic cable that emit light from the fiber optic cable into the antimicrobial solution.

15. A method for antimicrobial treatment of a user, comprising:
    retaining an antimicrobial solution in a solution holding apparatus;
    purposefully selecting a wavelength of light that reacts with the antimicrobial solution;
    providing the selected wavelength of light;
    utilizing a fiber optic cable on surface of the solution holding apparatus proximate the user to expose the antimicrobial solution to the light; and
    utilizing the solution holding apparatus to hold the lighted antimicrobial solution against the user.

16. The method of claim 15, wherein the solution holding apparatus includes a dental tray that retains the antimicrobial solution in a cavity on a side of the tray, the fiber optic cable is retained within the tray, and the solution holding apparatus holds the lighted antimicrobial solution against teeth of the user.

17. The method of claim 15, further comprising:
    shaping the solution holding apparatus before use to provide a dental tray that matches the teeth of the user; and
    positioning the fiber optic cable and a plurality of light terminations on the fiber optic cable within the tray, so that the light terminations emit light into the antimicrobial solution adjacent to the teeth of the user.

18. The method of claim 15, wherein the tray is shaped to hold the lighted antimicrobial solution against a tooth of the user, the antimicrobial solution is a gel that includes hydrogen peroxide (H2O2), and the selected wavelength of light is between 400 and 500 nanometers.

19. The method of claim 15, further comprising:
    warming the antimicrobial solution.

* * * * *